(12) United States Patent
Schoon et al.

(10) Patent No.: US 6,786,925 B1
(45) Date of Patent: Sep. 7, 2004

(54) DRIVER TOOL WITH MULTIPLE DRIVE GEAR LAYERS FOR HEART PROSTHESIS FASTENERS

(75) Inventors: Thomas G. Schoon, Cedar, MN (US); Eric S. Buchanan, Wyoming, MN (US)

(73) Assignee: St. Jude Medical Inc., St. Paul, MN (US)

( * ) Notice: Subject to any disclaimer, the term of this patent is extended or adjusted under 35 U.S.C. 154(b) by 8 days.

(21) Appl. No.: 09/692,129

(22) Filed: Oct. 19, 2000

Related U.S. Application Data

(63) Continuation-in-part of application No. 09/062,822, filed on Apr. 20, 1998, now Pat. No. 6,176,877, and a continuation-in-part of application No. 09/203,169, filed on Dec. 1, 1998, now Pat. No. 6,074,418, which is a continuation-in-part of application No. 09/062,822.

(51) Int. Cl.$^7$ .................................................. A61F 2/24
(52) U.S. Cl. ..................... 623/2.38; 623/2.11; 81/57.22
(58) Field of Search ................................. 623/2.1, 2.11, 623/2.14, 2.17, 2.18, 2.36–2.4, 900, 904, FOR 101

(56) References Cited

U.S. PATENT DOCUMENTS

| 3,143,742 A | 8/1964 | Cromie |
|---|---|---|
| 3,503,079 A | 3/1970 | Smith |
| 3,546,710 A | 12/1970 | Shumakov et al. |
| 3,574,865 A | 4/1971 | Hamaker |
| 3,587,115 A | 6/1971 | Shiley |
| 3,686,740 A | 8/1972 | Shiley |
| 3,996,623 A | 12/1976 | Kaster |
| 4,078,268 A | 3/1978 | Possis |
| 4,364,126 A | 12/1982 | Rosen et al. |
| 4,612,011 A | 9/1986 | Kautzky |
| 4,680,031 A | 7/1987 | Alonso |
| 4,705,516 A | 11/1987 | Barone et al. |
| 4,892,541 A | 1/1990 | Alonso |
| 5,032,128 A | 7/1991 | Alonso |
| 5,035,709 A | 7/1991 | Wieting et al. |
| 5,071,431 A | 12/1991 | Sauter et al. |
| 5,163,954 A | 11/1992 | Curcio et al. |
| 5,354,330 A | 10/1994 | Hanson et al. |
| 5,397,346 A | 3/1995 | Walker et al. |
| 5,562,729 A | 10/1996 | Purdy et al. |
| 5,607,470 A | 3/1997 | Milo |
| 5,716,370 A | 2/1998 | Williamson, IV et al. |
| 5,766,240 A | 6/1998 | Johnson |
| 5,776,188 A | 7/1998 | Shepherd et al. |
| 6,074,418 A | 6/2000 | Buchanan et al. ......... 623/2.11 |
| 6,113,632 A | 9/2000 | Reif |
| 6,143,025 A | 11/2000 | Stobie et al. |

FOREIGN PATENT DOCUMENTS

| CH | 307728 | * 8/1955 | ................ 81/57.22 |
|---|---|---|---|
| DE | 1180087 | 10/1964 | |
| DE | 35 07 109 A1 | 9/1986 | |
| EP | 0 119 357 A1 | 9/1984 | |
| EP | 0 544102 A1 | 6/1993 | |
| FR | 1 386 811 | 12/1964 | |
| GB | 1 600 506 | 10/1981 | |

(List continued on next page.)

*Primary Examiner*—David H. Willse
(74) *Attorney, Agent, or Firm*—Altera Law Group, LLC; Hallie A Finucane

(57) ABSTRACT

A driver tool drives multiple fasteners simultaneously through the outer ring of a heart valve component into the surrounding tissue annulus of a heart. The driver tool includes two stacked satellite gear layers that drive flexible shafts that simultaneously drive the fasteners into tissue surrounding the heart valve component. The flexible shafts from the second drive gear layer can pass through gaps between satellite gears in the first drive gear layer. The number of fasteners is increased while maintaining the mechanical advantage of the tool and the size of the tool, and reducing the concentration of stress in the tissue annulus.

22 Claims, 15 Drawing Sheets

FOREIGN PATENT DOCUMENTS

| | | |
|---|---|---|
| SU | 1 222 264 A | 8/1983 |
| WO | WO 87/05489 | 9/1987 |
| WO | WO 91/14408 | 10/1991 |
| WO | WO 96/03925 | 2/1996 |
| WO | WO 96/12452 | 5/1996 |
| WO | WO 97/09948 | 3/1997 |
| WO | WO 97/30659 | 8/1997 |

* cited by examiner

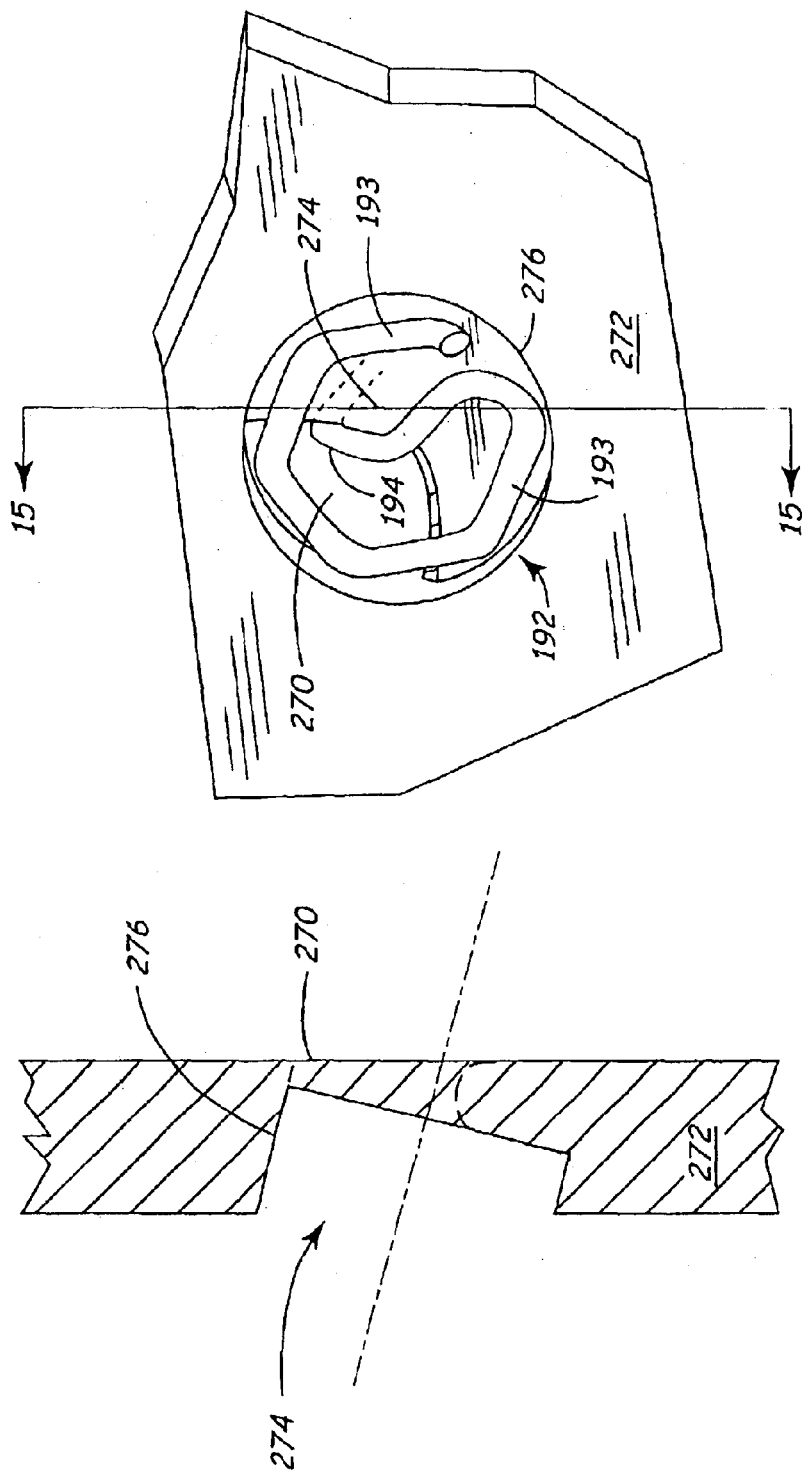

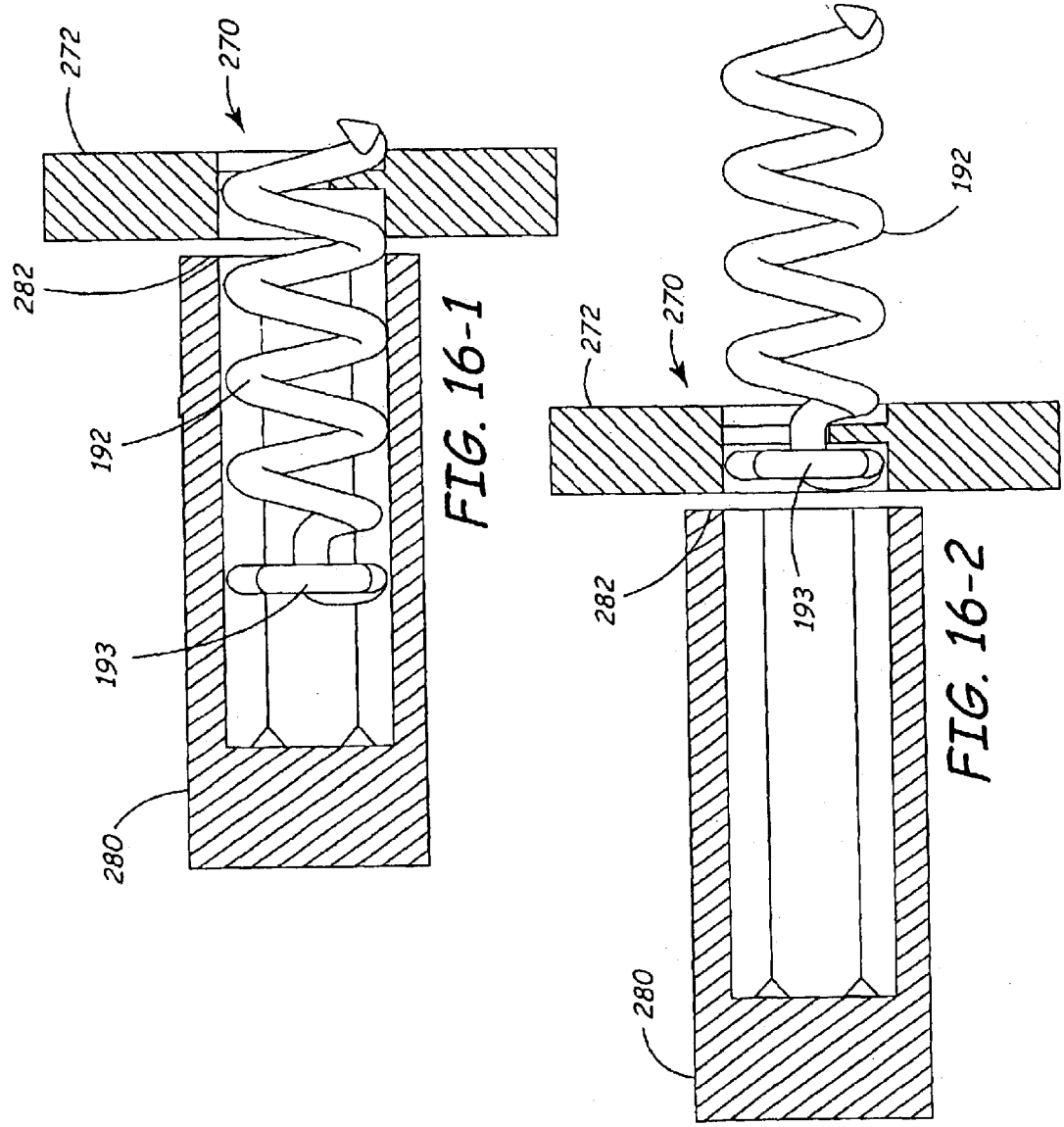

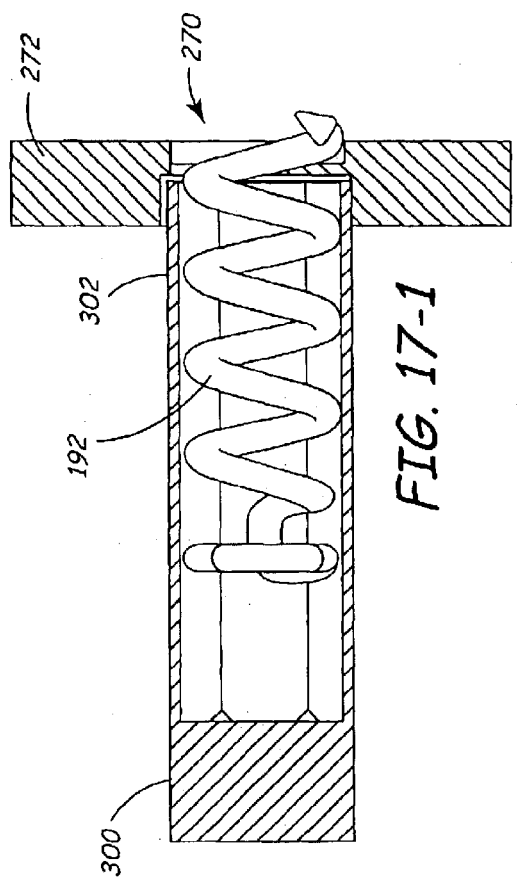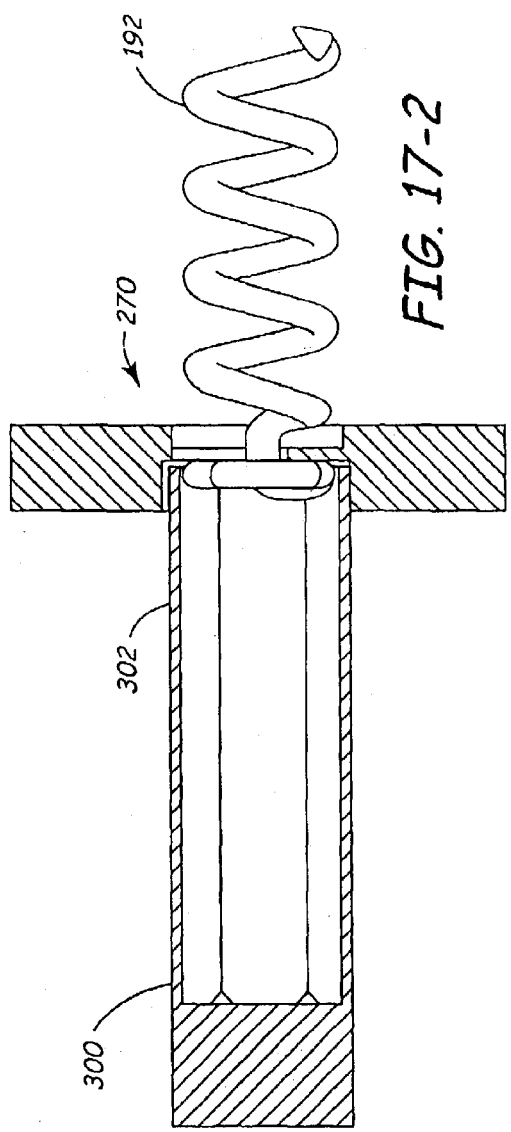

DRIVER TOOL WITH MULTIPLE DRIVE GEAR LAYERS FOR HEART PROSTHESIS FASTENERS

CROSS-REFERENCE TO RELATED APPLICATIONS

This application is a continuation-in-part of application Ser. No. 09/062,822, filed Apr. 20, 1998, now U.S. Pat. No. 6,176,877, and is a continuation-in-part of application Ser. No. 09/203,169, filed Dec. 1, 1998, now U.S. Pat. No. 6,074,418, which is a continuation-in-part of application Ser. No. 09/062,822 (filed Apr. 20, 1998, now U.S. Pat. No. 6,176,877).

FIELD OF THE INVENTION

The present invention relates to mechanical heart valve prostheses. More specifically, the invention relates to a driver tool for attaching and implanting heart valve prostheses.

BACKGROUND OF THE INVENTION

Implantable mechanical heart valves are used for replacement of defective valves in hearts of patients. One common implantation method employs a sewing ring or suture cuff which is attached to and extends around the outer circumference of the mechanical valve orifice. The sewing cuff is made of a biocompatible fabric suitable for allowing a needle and suture to pass therethrough. The cuffs are typically sutured to a tissue annulus that is left when the surgeon removes the native valve from the patient's heart. The sutures are tied snugly, thereby securing the valve to the heart.

Sewing cuffs are labor intensive, difficult to manufacture and are difficult to secure to the valve orifice. Further, suturing the cuff to the tissue annulus is time consuming and cumbersome. The complexity of suturing requires a patient to be on cardiopulmonary bypass for a lengthy period. It is also desirable to provide a large lumen through the valve orifice relative to the overall valve diameter for blood flow. However, techniques for attaching the sewing cuff to the valve orifice typically require that the area of the valve lumen be reduced to accommodate an attachment mechanism. For example, the sewing cuff is typically retained between two rims of the valve orifice. One of the rims normally defines the outside diameter of the valve orifice and thus limits the size of the valve lumen.

Another technique for attaching heart valves uses a series of pins which pierce the tissue annulus of the heart. The pins are crimped or bent, thereby locking the valve to the heart tissue and preventing the valve from separating from the heart. This technique is described in U.S. Pat. Nos. 3,574,865 and 3,546,710. Another technique for attaching a prosthetic heart valve to the heart tissue is shown in U.S. Pat. No. 4,705,516 in which an outer orifice ring is sutured to the tissue annulus and an inner orifice ring is then screwed into the outer orifice ring. However, the rings are not locked together and may become unscrewed after extended use.

Implantable heart valves can also use helical fasteners to hold them securely to surrounding tissue in the body. The use of helical fasteners or screws is disclosed in the above cited application Ser. No. 09/062,822. However, access to the multiple helical fasteners used with an implant tool one at a time can be difficult and time consuming. The fasteners face in different directions and a simple tool must be positioned multiple times to approach the implantable heart valve component from several difficult angles around the heart, some of which may be obstructed by adjoining tissue. A tool which solves this problem and simultaneously drives multiple fasteners using satellite gears is disclosed in U.S. Pat. No. 6,074,418. This simultaneous driver tool, however, is limited in the number of fasteners that can be driven conveniently. As the number of fasteners increases, the number of satellite gears increases as well, and the satellite gears must be made smaller to fit all of them in the tool housing. There is a minimum gear tooth size that will allow sufficient mechanical contact between the central gear and the satellite gears. Consequently, there is a minimum satellite gear diameter, which means there is a maximum number of gears that will fit in the tool housing diameter. Also, the gear ratio or mechanical advantage for the tool decreases as the satellite gears get smaller and the torque needed to drive the fasteners increases.

In some applications, however, a greater number of fasteners is desired to distribute the securing forces over a larger number of fasteners to lower concentrations of securing force in the small portions of tissue annulus engaged by each of the helical fasteners, without adversely affecting the mechanical advantage of the tool. In some applications, a greater number of fasteners is desired to decrease the spacing between attachment points.

SUMMARY OF THE INVENTION

The present invention is useful in implanting a prosthetic heart valve in a heart with fasteners. The heart valve includes an outer ring for coupling to a tissue annulus of a heart. An inner orifice ring includes an occluding mechanism movable between an open position, which allows blood flow through the lumen, and a closed position which prevents blood flow through the lumen. The inner orifice ring is adapted to be coupled to the outer orifice ring after the outer orifice ring has been attached to the tissue annulus.

The outer ring is attached to the tissue annulus by helical fasteners and is coupled to the inner orifice ring by a snap fit.

In the present invention, a driver tool drives multiple fasteners simultaneously through the outer ring of a heart valve component into the surrounding tissue annulus of a heart.

The driver tool includes a tool housing that has a distal housing end couplable to the heart valve component and has a proximal housing end spaced away from the distal housing end along an axis.

The driver tool includes a central shaft in the tool housing that has a proximal shaft end that can be coupled to a driving force such as an electric motor or an operator's hand. The central shaft extends to a distal shaft end near the heart valve component.

The driver tool includes a first satellite gear drive layer that has a first drive gear engaging the distal shaft end and a first plurality of satellite gears at first spaced circumferential positions meshing with the first drive gear. The first satellite gear drive layer also has a first plurality of flexible shafts connected to the first plurality of satellite gears and adapted to drive a first portion of the fasteners.

The driver tool also includes a second satellite gear drive layer that has a second drive gear engaging the distal shaft end and a second plurality of satellite gears at second spaced circumferential positions meshing with the second drive gear. The second satellite gear drive layer also has a second plurality of flexible shafts connected to the second plurality of satellite gears and arranged to drive a second portion of the fasteners.

Preferably, a first (lower) plurality of satellite gears are separated from one another by gaps, and the second (upper) plurality of satellite gears are circumferentially offset to align with the gaps in the first row. In this preferred arrangement, the second plurality of flexible shafts pass through the gaps, and each upper and lower flexible shaft drives a corresponding fastener simultaneously.

BRIEF DESCRIPTION OF THE DRAWINGS

FIG. 15 is an illustration of a fastener with a generally straight portion engaging a hole in an outer orifice ring.

FIG. 16 is a cross-sectional illustration of a driver tip, a fastener and a hole in an outer orifice ring, before (FIG. 16-1) and after (FIG. 16-2) driving the fastener.

FIG. 17 is a cross-sectional illustration of a driver tip, a fastener and a hole in an outer orifice ring, before (FIG. 17-1) and after (FIG. 17-2) driving the fastener.

DETAILED DESCRIPTION OF THE ILLUSTRATED EMBODIMENTS

The driver tool shown in U.S. Pat. No. 6,074,418 is limited in the number of fasteners that can be driven simultaneously for a comfortable level of operator applied torque, adequate fastener torque and outer housing diameter. As the number of fasteners increases, the number of satellite gears increases as well, and the satellite gears must be made smaller to fit in the tool housing. There is a minimum gear tooth size that can transfer the needed torque, which means there is a maximum number of gears that will fit in the housing. The gear ratio or mechanical advantage for the tool decreases as the satellite gears get smaller and the torque needed to drive the fasteners increases for the operator.

In the present invention, a driver tool has two or more satellite gear drive layers stacked inside a tool housing to simultaneously drive fasteners into a heart valve prosthesis component. By stacking the satellite gears in layers, the number of satellite gears is increased relative to the number that can be effectively used with the single layer arrangement shown in the above cited U.S. Pat. No. 6,074,418. The diameter of the tool housing can be kept small and easy to grip, and the mechanical advantage or gear ratio can be kept high so that the tool handle is easy to turn, and gear tooth size can be kept large enough to transmit the needed torque.

The greater number of fasteners distributes the securing forces over a larger number of fasteners and lowers concentrations of securing force in the small portions of the tissue annulus engaged by each of the fasteners. This also minimizes the likelihood of blood leaking around the valve prosthesis.

Figure 1:
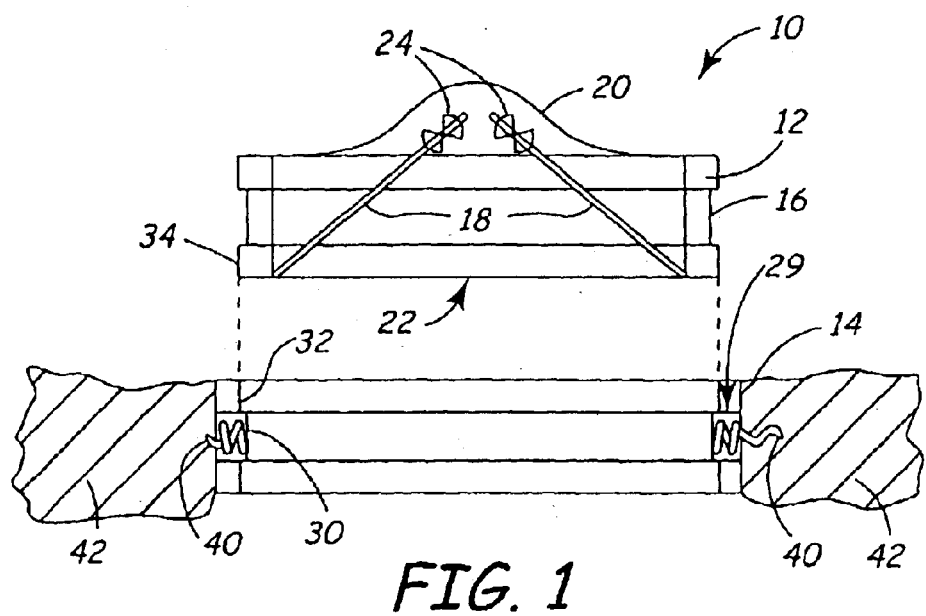
FIG. 1 is an exploded cross-sectional view of a prosthetic heart valve.
Figure 2:
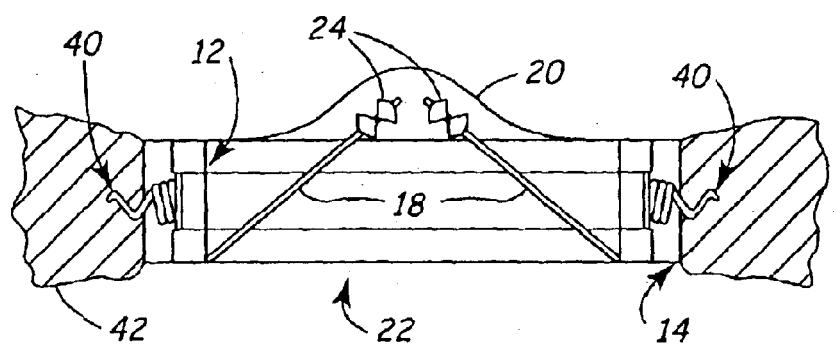
FIG. 2 is a cross-sectional view of the heart valve of FIG. 1.

A heart valve prosthesis 10 shown in FIGS. 1–2 includes inner orifice ring 12 and outer orifice ring 14. FIG. 1 is a side cross-sectional exploded view of valve 10 and FIG. 2 is a side assembled cross-sectional view of valve 10.

Inner orifice ring 12 includes locking recess 16 (or, in another embodiment, a ridge) formed around its outer circumference. Leaflets (or occluders) 18 provide an occluding mechanism and are pivotably coupled to ring 12. Leaflets or occluders 18 move between an open position (not shown) and a closed position as shown in FIGS. 1 and 2 in which flow of fluid through lumen 22 is blocked. Leaflets 18 rotate within pivots 24. Valve 10 includes pivot guards 20. In one preferred embodiment, inner ring 12 comprises a prosthetic heart valve available from St. Jude Medical, Inc. of St. Paul, Minn., without a sewing cuff carried thereon. However, in some embodiments it may be preferable to use a specially designed inner ring 12. The inner ring 12 can be adapted to fit with outer orifice rings such as an outer ring described in connection with FIG. 12 as well as other outer orifice rings described below.

Outer orifice ring 14 includes locking ridge 30 (or, in another embodiment, a recess) formed on an inner annulus circumference thereon. Inner diameter 32 of ring 14 is sized to have approximately the same radius as outer diameter 34 of inner ring 12. Similarly, locking ridge 30 of outer ring 14 substantially conforms to locking recess 16 of inner ring 12. Locking recess 16 and locking ridge 30 cooperate to provide a ring coupling mechanism adapted to couple the outer orifice ring to the inner orifice ring. Outer orifice ring 14 also includes tissue annulus attachment locking mechanism 40 which, in one preferred embodiment, comprises helical screws carried through holes 29 around the circumference of outer ring 14. Other types of attachment mechanisms include staples, pins, rivets, "nails", barbs, hooks, etc. These mechanisms could be coupled to or integral with the outer orifice ring. As illustrated in FIGS. 1 and 2, locking mechanism 40 attaches to the native heart tissue annulus 42 of the patient.

Figure 3:
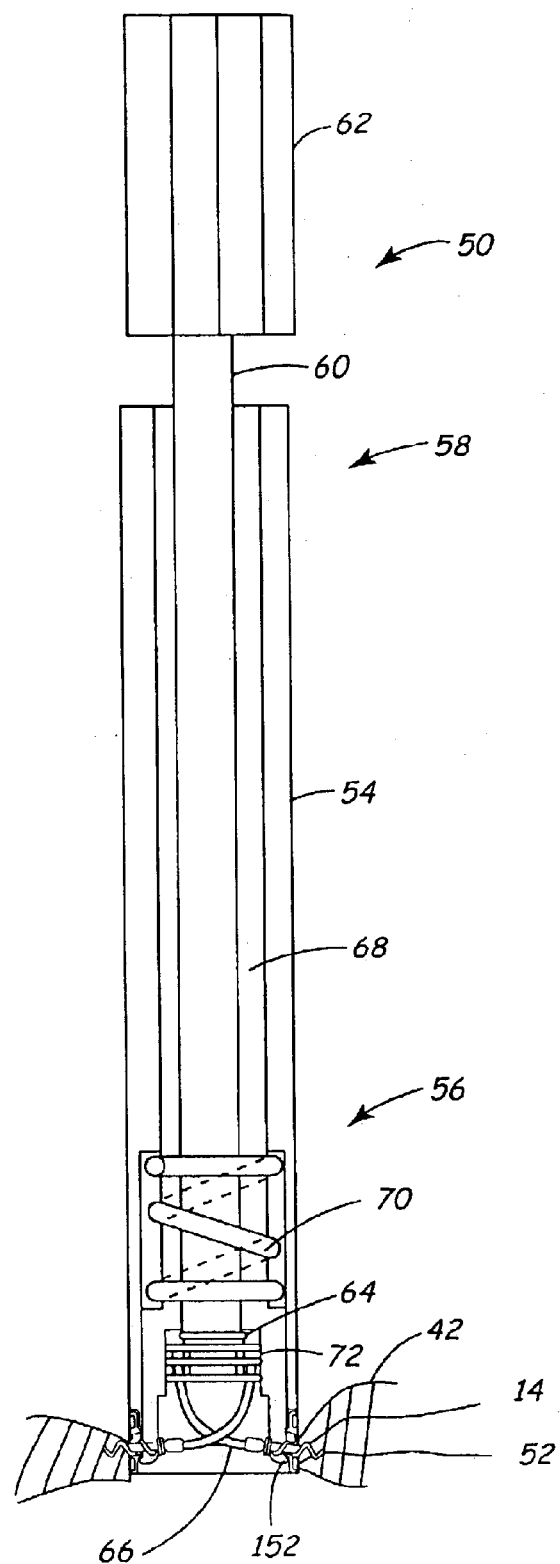
FIG. 3 is a side cross-sectional view of first embodiment of an implantation tool for implanting the heart valve prosthesis shown in FIGS. 1 and 2.

In FIG. 3, driver tool 50 is shown engaging outer orifice ring 14 of a two piece prosthetic heart valve. Driver tool 50 couples to helical fasteners 52 which pass through holes 29 (FIG. 1), 80 (FIG. 4) in outer ring 14. Helical fasteners 52 can be any fasteners that advance along a central axis by being turned about that axis, anything that goes in by twisting, e.g. even a screw. Examples of suitable helical fasteners are described below and in the above-cited application Ser. No. 09/062,822 and U.S. Pat. No. 6,074,418.

Helical screw fasteners 52 attach outer orifice ring 14 to tissue annulus 42 during an implantation procedure using driver tool 50. Driver tool 50 includes tool housing 54, which is generally cylindrical in shape, or round in cross section. Tool housing 54 extends from distal end 56, which engages outer orifice ring 14, to proximal end 58 spaced away from the distal end 56. A central shaft 60 has a handle 62 at proximal end 58 that can receive a twisting or driving force for transmission to helical screw fasteners 52.

Handle 62 can also be actuated or pulled away from the proximal end 58 to disengage driver tool 50 from helical screw fasteners 52 after they have been advanced. The handle 62 is lifted relative to tool housing 54 while the surgeon holds tool housing 54. This lifting action first lifts central shaft 60, compresses spring 64, disengaging helical screw fasteners 52 from the drive ends 152 attached to flexible shafts 66 of the tool 50. When spring 64 is fully compressed, lifting force is transferred through the compressed spring 64 to tube 68. When the handle is lifted further, tube 68 lifts relative to tool housing 54, compressing spring 70 while tool housing 54 remains in contact with outer orifice ring 14 at surface 78. Spring 70 is made stiffer than spring 64 so that the flexible shafts 66 disengage from the helical screw fasteners 52 before tube 68 lifts to release outer orifice ring 14 from driver tool 50. Tool housing 54 moves toward outer ring 14 while other parts of driver tool 50 retract or move away from outer ring 14. The tool 50 is thus fully disengaged from outer ring 14 and helical screw fasteners 52 after use.

As explained in more detail below, driver tool 50 includes a two layer satellite gear drive arrangement 72 which allows an increased number of screw fasteners 52 to be used and reduces the securing forces concentrated in portions of the tissue annulus 42 around the screw fasteners.

Figure 4:
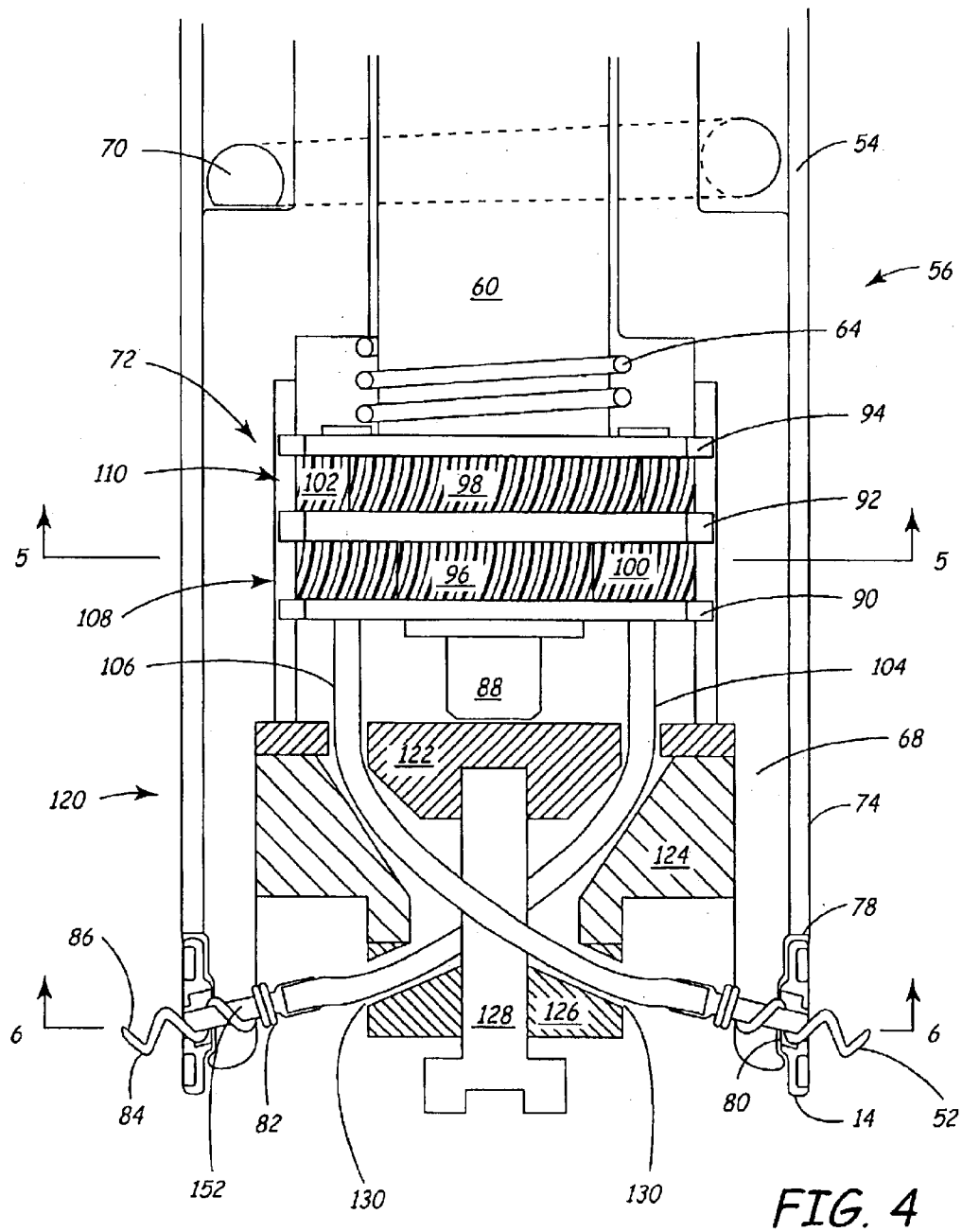
FIG. 4 is an enlarged side cross-sectional view of a first embodiment of a distal end of the tool illustrated in FIG. 3.

In FIG. 4, a first embodiment of distal end 56 of FIG. 3 is shown in more detail. At distal end 56, cylindrical end 74 of tool housing 54 abuts outer orifice ring 14. Helical screw fasteners 52 pass through holes 80 in outer orifice ring 14 and into tissue annulus 42 (FIG. 3). Typically there are approximately sixteen helical fasteners 52 although any number can be used, each passing through a separate hole 80 in outer ring 14. Helical screw fasteners 52 can be formed of metal wire compatible with implantation, and have a hub portion 82 which is wound in a polygonal shape, typically a hexagon, and the remainder 84 of the helical fastener 52 is wound in a helix with a sharp point 86 at the end. In another embodiment, the last coil of the hub portion 82 turns into the center of the coil.

In FIG. 4, central drive shaft 60 couples to a two layer satellite gear drive arrangement 72. The embodiment shown in FIG. 4 is similar in some respects to a single layer arrangement shown in FIG. 12 of U.S. Pat. No. 6,074,418 to Buchanan and Anderson. Central drive shaft 60 is narrowed to form a gear shaft 88 on its end. Gear plates 90, 92, 94 are assembled on gear shaft 88 so that gear shaft 88 is free to spin relative to gear plates 90, 92, 94. Drive gears 96, 98 are attached to gear shaft 88 so that gear shaft 88 drives the drive gears 96, 98.

Figure 5:
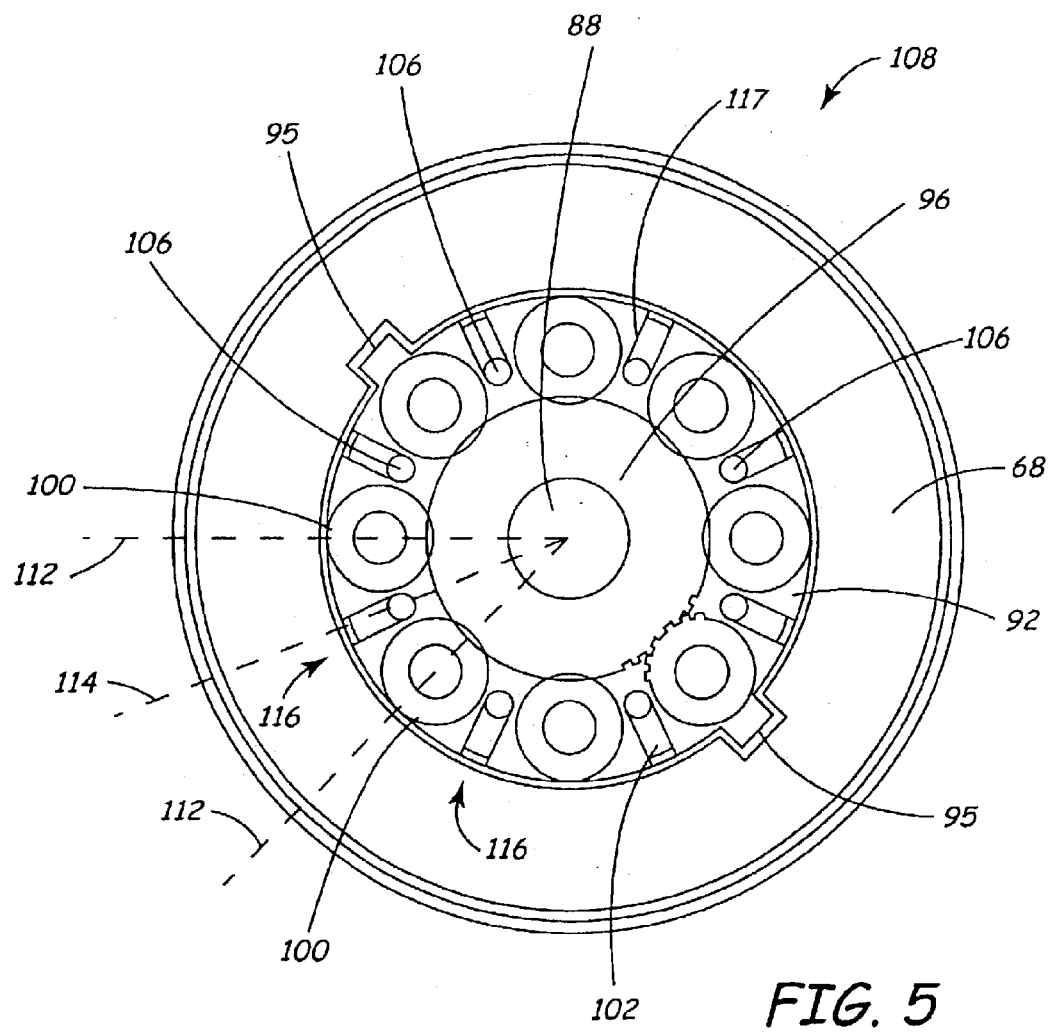
FIG. 5 is a sectional view taken along line 5—5 in FIG. 4.

A number of first satellite gears 100 are assembled between plates 90 and 92, engaging or meshing with first drive gear 96. Eight gears 100 are illustrated in FIG. 5, but any number can be used, depending on the needs of the application. A number of second satellite gears 102 are assembled between plates 92 and 94, engaging or meshing with second drive gear 98. The number of first satellite gears 100 can be different from the number of second satellite gears 102, if desired. Each of eight first satellite gears 100 is connected to one of eight first flexible shafts 104. Each of eight second satellite gears 102 is connected to one of eight second flexible shafts 106. The first drive gear 96, the first satellite gears 100, and the first flexible shafts 104 together comprise a first satellite gear drive layer 108. The second drive gear 98, the second satellite gears 102 and the second flexible shafts 106 comprise a second satellite gear drive layer 110.

A distributor 120 is disposed in the distal end 56 of the tube 68. Distributor 120 includes an upper distributor plate 122, a central distributor housing 124 and a bottom distributor plate 126 assembled on a central distributor pin 128. As shown in FIG. 4, the distributor 120 provides a plurality of guide passageways 130. Each one of the first and second plurality of flexible shafts 104, 106 pass through a corresponding one of the guide passageways 130.

The outer orifice ring 14 has fastener holes 80 at circumferentially spaced hole positions and the guide passageways 130 have guide passageway ends that are aligned with the hole positions. The fastener holes 80 can be axially staggered, if desired, and ends of the guide passageways 130 are correspondingly axially staggered. The staggering provides increased spacing for the guide passageways 130 and fastener holes 80. For larger size valves, or when fewer fasteners are used, the staggering can be omitted and the fastener holes 80 can be arranged along a generally straight circular path.

Each flexible shaft 104, 106 makes a turn inward of about 60 to 90 degrees (preferably between 75 and 85 degrees) and extends across a central region around the central distributor pin 128 to drive ends 152 which engage the helical screw fasteners 52. Central distributor pin 128 separates the shafts 104, 106 to help prevent tangling of the flexible shafts 104, 106.

At distal end 56, the plurality of plates 90, 92, 94 are arranged to support the first and second plurality of satellite gears 100, 102 in gear layers 108, 110. Plates 90, 92 have a plurality of radial slots 117 extending to outer edges of the plates 90, 92 as illustrated below in FIG. 5 or as shown below at 156 in FIG. 8. Each satellite gear 100, 102 is permanently assembled to a corresponding one of the flexible shafts 104, 106 to form a drive assembly, and each radial slot 117 is arranged to accept a corresponding one of the drive assemblies.

The driver tool illustrated in FIGS. 3,4 or 7 can be used with various types of drive ends and fasteners, including those illustrated in FIGS. 9, 10, 11 below.

FIG. 5 illustrates a sectional view along line 55 in FIG. 4 through the first satellite drive gear layer 108. The first satellite gears 100 are at first spaced circumferential positions 112 around the first drive gear 96. The second satellite gears 102 are at second spaced circumferential positions 114 around the second drive gear 98 (not shown). The second spaced circumferential positions 114 are offset from the first spaced circumferential positions 112. The first satellite gears 100 are separated from one another by gaps 116, and the second flexible shafts 106 pass through the gaps 116. The second satellite gears 102 are circumferentially aligned with the gaps 116.

The first flexible shafts 104 and the second flexible shafts 106 preferably are driven simultaneously.

Plates 90, 92, 94 are provided with tabs such as tabs 95 illustrated in FIG. 5 that resist rotation of plates 90, 92, 94 relative to tube 68.

Figure 6:
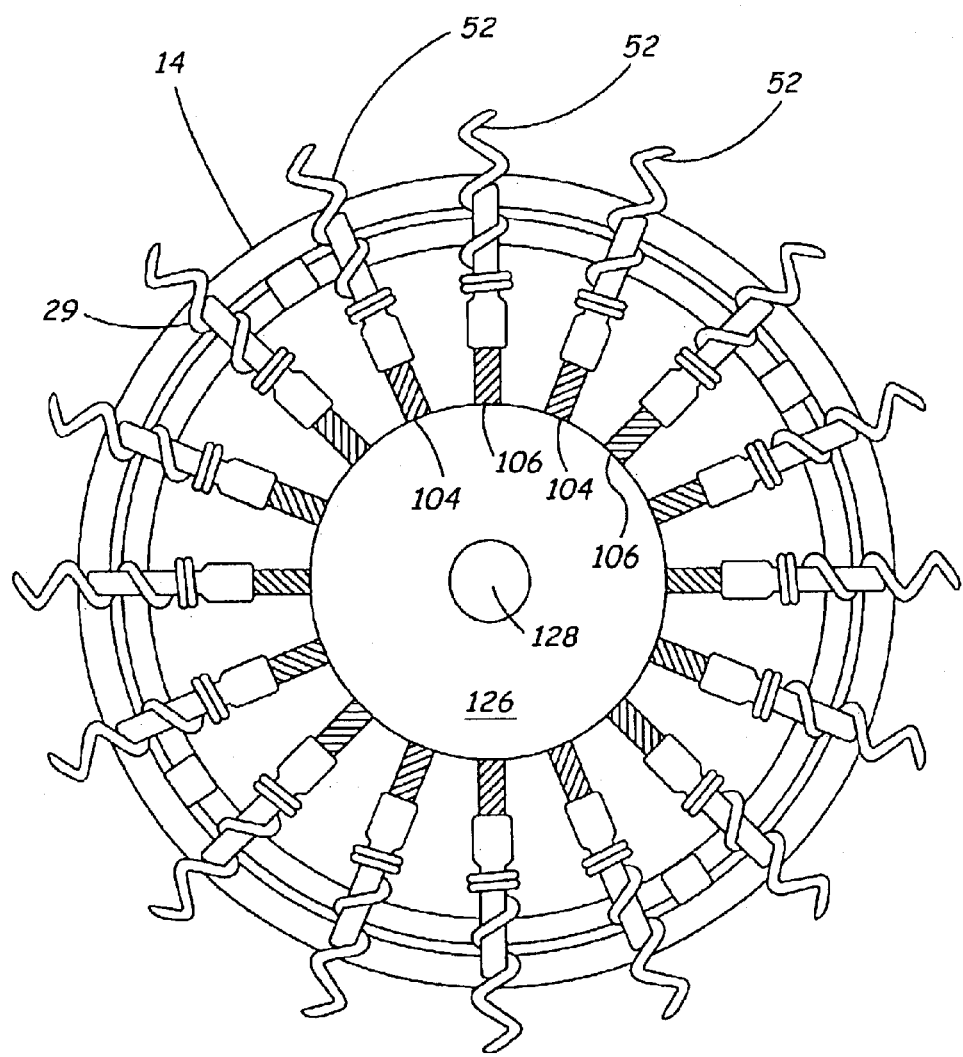
FIG. 6 is a sectional view taken along line 6—6 in FIG. 4.

FIG. 6 is a sectional view taken along line 6—6 in FIG. 4. FIG. 6 illustrates 16 helical fasteners 52 at circumferentially spaced positions around the bottom distributor cap 126. There are 8 flexible shafts 104 from the first or lower satellite gear drive layer 108 and there are 8 flexible shafts 106 from the second or upper satellite gear drive layer 110.

Figure 7:
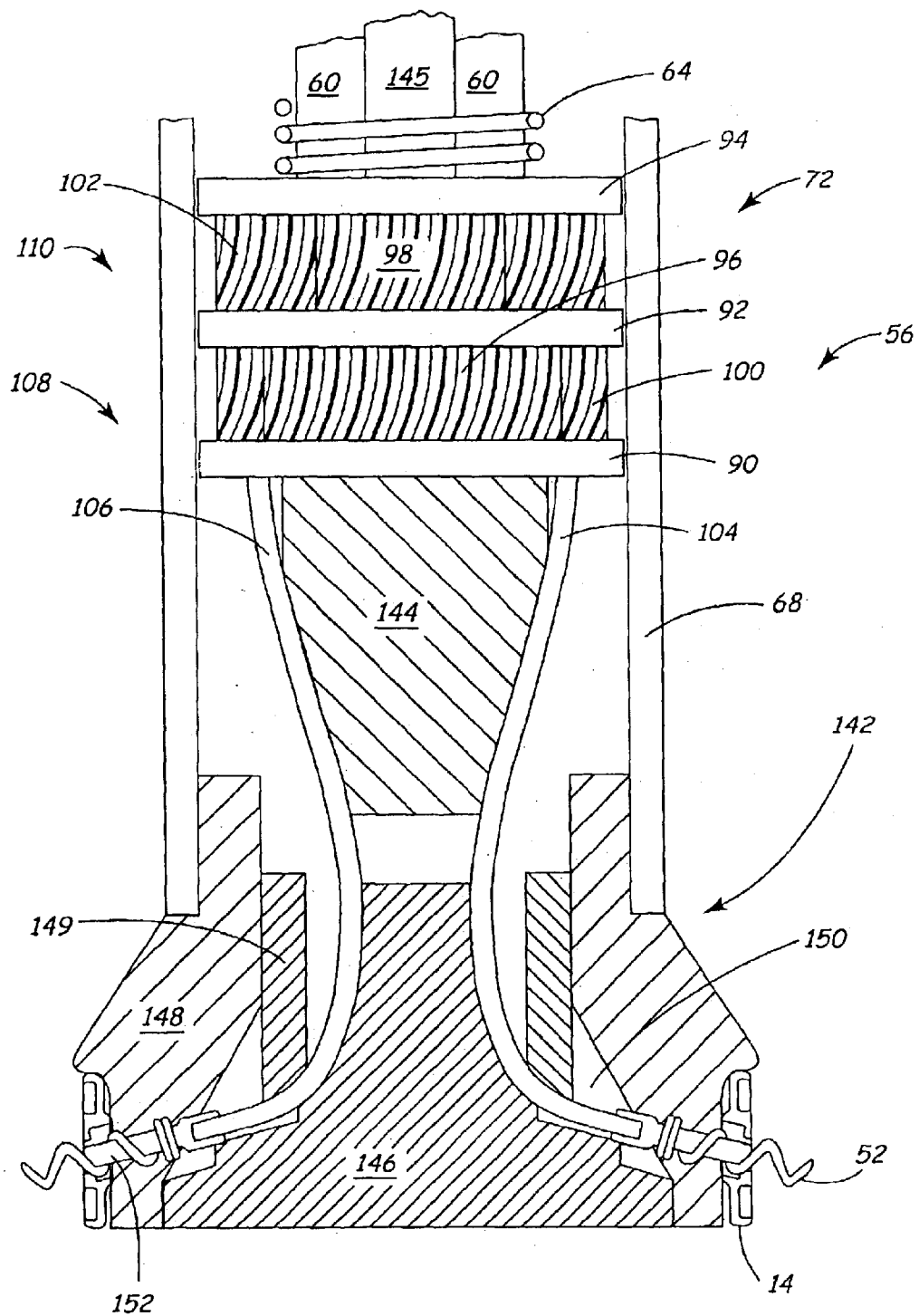
FIG. 7 is a side cross-sectional view of a second embodiment of a distal end of the tool illustrated in FIG. 3.

FIG. 7 is a side cross-sectional view of a second embodiment of a distal end 56 of the tool illustrated in FIG. 3. The embodiment of distal end 56 shown in FIG. 7 is similar to the embodiment shown in FIG. 4 except that a different distributor 142 is used in FIG. 7 that turns each of the flexible shafts 104, 106 radially outward, avoiding having the flexible shafts 104, 106 pass through a central region around the central distributor pin 128. Reference numbers used in FIGS. 4–6 are also used in FIG. 7 to identify similar or identical components. In FIG. 7, distributor 142 comprises a truncated cone-shaped projection 144 upon which drive gears 96, 98 and shaft 145 are assembled. Distributor 142 also comprises shaft support cone 146, cylindrical shaft retainer 149 and shaped distributor wall 148. The outer surfaces of projection 144 and cone 146 follow the natural curvature of flexible shafts 104, 106, and support the flexible shafts from inward displacement. The space between shaft support cone 146 and shaft retainer 149 provides a guide slot 150. The guide slot 150 serves as a guide passageway for the flexible shafts 104, 106. Each one of the first and second plurality of flexible shafts 104, 106 pass through guide slot 150.

In this embodiment, when central shaft 60 retracts, compressing spring 64, the satellite gear drive arrangement 72 is pulled toward proximal end 58. Flexible shafts 104 and 106 slide through guide slots 150 causing drive ends 152 to disengage from the central axis of helical screw fasteners 52. This releases outer ring 14 from distributor wall 148. Outer ring 14 is retained on the tool by the driver tips 152 and the helical screw fasteners 52 until the driver tips 152 are retracted.

In the embodiment illustrated in FIG. 7, there are relatively fewer moving parts compared with the embodiment illustrated in FIGS. 4–6. In FIG. 7, the tube 68, support cone 146, shaped distributor wall 148 and cylindrical shaft retainer 149 can all be assembled in fixed relationship to one another, so there is no relative motion between them during use. Outer orifice ring 14 is retained on distributor wall 148 by helical fasteners 52. Only one spring 64 is used in this embodiment, and a spring like spring 70 of FIG. 4 is not needed.

Figure 8:
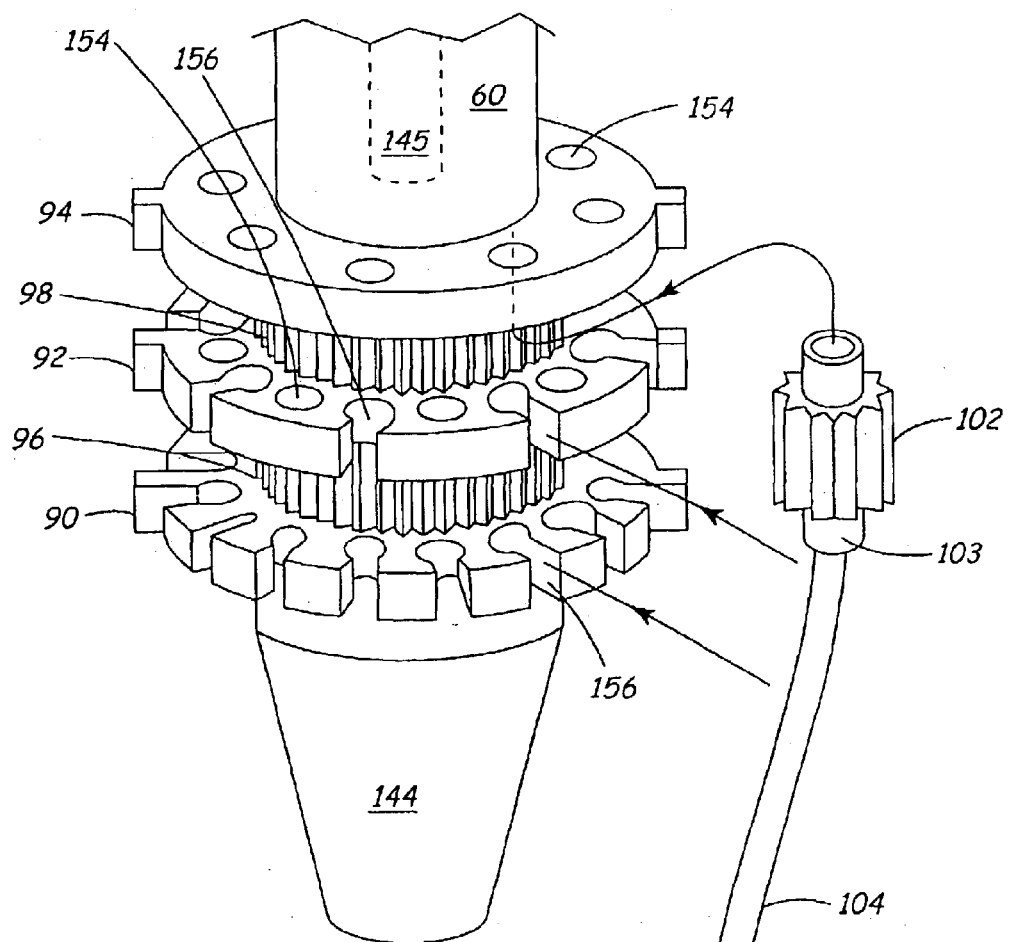
FIG. 8 is an exploded view of a portion of a satellite gear drive of the implantation tool of FIG. 7.

FIG. 8 illustrates an exploded view of a portion of the satellite gear drive of the implantation tool of FIG. 7. Gear plate 94 is provided with through holes 154, and gear plate 90 is provided with radial slots 156, and gear plate 92 is provided with alternating radial slots 156 and through holes 154, as illustrated in FIG. 8. The radial slots 156 extend to the outer edges of the plates 90, 92. The gear plates 90, 92, 94 are loosely assembled on the shaft 145 of cone 144, interleaved with drive gears 96, 98. During assembly of the tool, the sixteen driver tips 152 are first assembled in the distributor components 146, 148 (FIG. 7). Central shaft 60 is then coupled (for example, glued, pressed, pinned) to shaft 145 extending from cone 144, so the plates 90,92, 94 can spin, and so that rotation of shaft 60 causes rotation of shaft 145 and the drive gears 96, 98. The satellite gears 100, 102 can then be inserted between the gear plates 90, 92, 94. Then the bottom collar 103 of each satellite gear 100, 102 can be snapped in place in one of the slots. Alternatively, the satellite drive gear assembly could be built sequentially from bottom to top. Gear plate 90 slides onto the shaft 145 of cone-shaped projection 144. Drive gear 96 is pressed onto shaft 145, leaving gear plate 90 with a loose fit. First satellite gears 100 are installed on gear plate 90 and trapped by gear plate 92. Drive gear 98 is pressed onto shaft 145, leaving gear plate 92 with a loose fit. Second satellite gears 102 are installed on top of gear plate 92 with their tops trapped by gear plate 94. Central shaft 60 is pressed, glued, pinned or fastened onto the shaft 145 of cone 144.

Regardless of the assembly sequence used for the tool illustrated in FIGS. 7 and 8, shaft 145 is free to spin relative to plates 90, 92, 94 so that shaft 145 can drive the drive gears 96, 98. Cone 144 is also driven by shaft 145. Drive gears 96, 98, in turn, drive satellite gears 100, 102 which drive flexible shafts 104, 106.

The rest of the tool is then assembled, and it is ready for use after sterilization. This alternative is preferred since radial slots 156 can be eliminated from gear plates 90 and 92. Only through holes 154 are needed to securely hold satellite gears 100 and 102 in place. Eliminating the snap fit of collar 103 to slots 156 increases the strength of the assembly.

Figure 9:
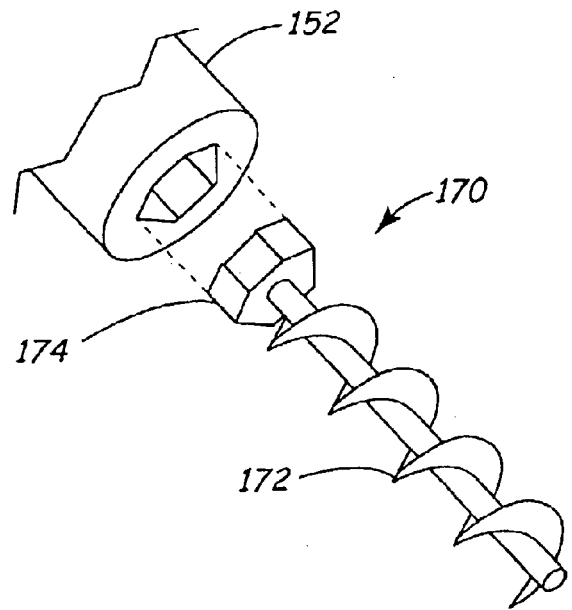
FIG. 9 is an exploded perspective view of an auger-shaped helical fastener.

FIG. 9 is a perspective view of an auger-shaped helical fastener 170 that can be used with the tools described above. The fastener 170 has an auger-shaped first portion 172 adapted to engage the tissue annulus and an M-sided second portion 174. When fastener 170 is used, the drive ends 152 of the flexible shafts 104, 106 have an M-sided socket for engaging the M-sided second portion 174. Alternatively, the fastener 170 can have an M-sided socket and the ends 152 can have M-sided projecting portions similar to M-sided second portion 174. The number of sides M can be in the range of about 3 to 8, and is preferably 6. The M-sided projection and the M-sided socket slidingly engage each other while the fastener 170 is being driven or twisted, and then slide apart for disengagement.

Figure 10:
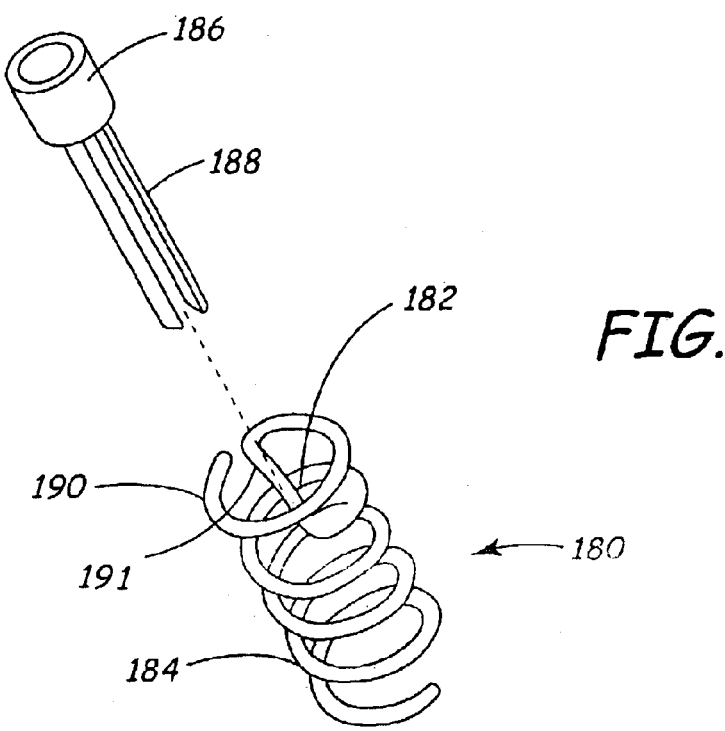
FIG. 10 is an exploded perspective view of a round helical fastener with a generally straight section.

FIG. 10 is a perspective view of a round helical fastener 180 with a generally straight axial section 182 that can be used with the tools described above. Fastener 180 has a helical first portion 184 wound around a helical axis, a generally straight second portion 182 extending along the helical axis, and a flat (non-helical) generally circular head portion 190 perpendicular to the helical axis. The head portion 190 includes a small radial portion 191 that joins to the generally straight section 182.

The driver end 186 of a flexible shaft 102, 104 has a slotted shaft end 188 that selectively drives the fasteners 180. Driver end 186 can be used with the tools illustrated in FIGS. 4, 8 in place of driver tips 152, for example. The slotted shaft end 188 engages and drives the radial portion 191. The generally straight second portion 182 rotates in hole 80 of outer orifice ring 14. This allows the screw to pull the tissue annulus tightly against the outer orifice ring 14 to minimize the gap between the tissue annulus and the outer orifice ring. The fastener 180 selectively advances relative to the fastener hole in an outer orifice ring 14 when the helical portion passes through the fastener hole. The fastener 180 does not advance relative to the fastener hole when the flat portion 190 engages the fastener hole. The fasteners 180 do, however, advance relative to the tissue annulus when the generally straight second portions 182 engage the fastener hole. When the generally straight second portions 182 engage the fastener hole, the fasteners rotate in the fastener holes. This arrangement allows the tissue annulus to be pulled more snugly against the outer orifice ring 14.

Figures 1, 11:
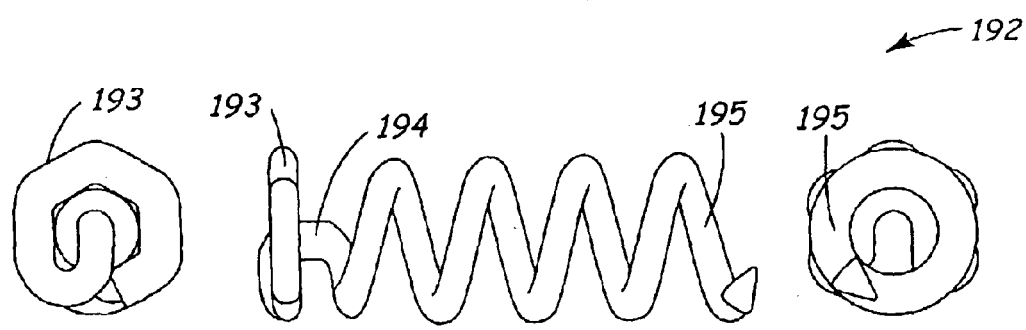
FIG. 11 is an illustration of multiple-sided helical fasteners set forth as FIGS. 11-1 and 11-2.
Figures 2, 11:
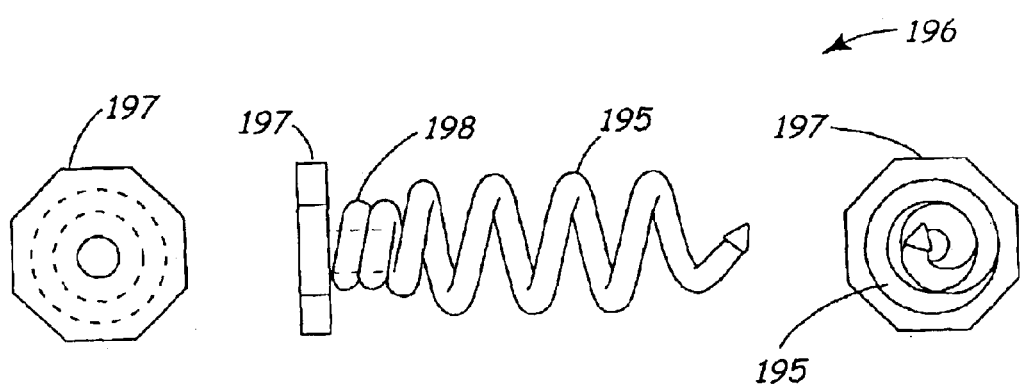

FIG. 11 is an illustration of two alternative helical fasteners 192, 196. Fastener 192 is formed completely of wire and has a round spiral shaped main body 195 that is joined with an N-sided polygonal shaped hub portion 193. The main body 195 is either affixed to or integrally formed with the hub portion 193 of fastener 192 by a generally straight section 194. Generally straight section 194 can rotate in a fastener hole without advancing in the fastener hole while the round spiral shaped main body 195 rotates, drawing the tissue closely to the ring as explained in more detail below in connection with FIGS. 15–17.

Fastener 196 is formed partially of wire and has a round spiral shaped main body 195. Fastener 196 includes an N-sided polygonal shaped solid hub portion 197 that is machined in a shape that is similar to a hex-headed cap screw. A wrapped portion of wire 198 that is joined to the main body 195 is tightly wrapped around a round shaft portion of solid hub portion 197. The wrapped portion of wire 198 extends generally straight along the major axis of the fastener 196. The wrapped portion of wire 198 can rotate in a fastener hole without advancing in the fastener hole while the round spiral shaped main body 195 rotates, drawing the tissue closely to the ring as explained in more detail below in connection with FIGS. 15–17.

A flexible shaft 102, 104 with an N-sided socket (as illustrated in FIGS. 9, 16 or 17) can engage the fastener 192 (or 196) and drive the fastener 192 (or 196). N is a number selected in the range of 3 to 8, and is preferably 6 as illustrated.

Figure 12:
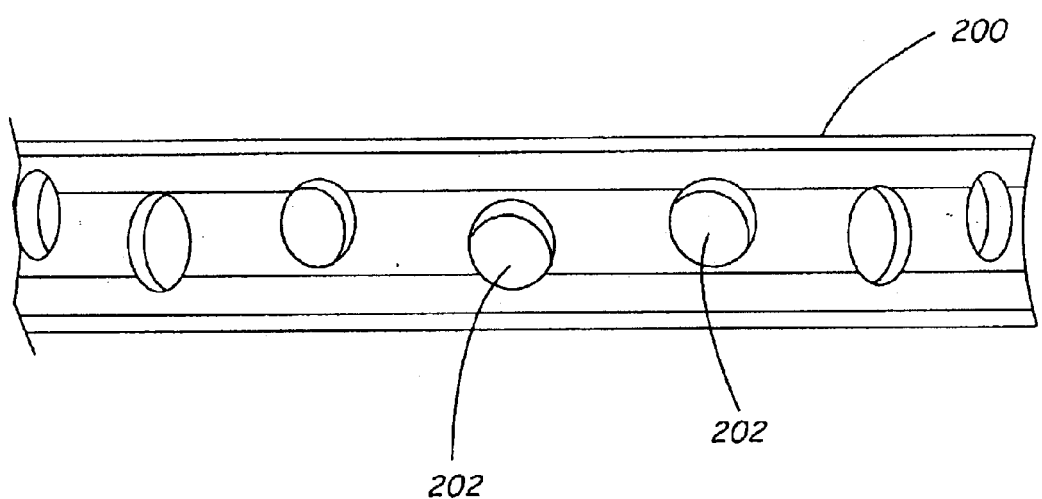
FIG. 12 is an illustration of an outer orifice ring with 16 fastener holes.

FIG. 12 illustrates an outer orifice ring 200 with 16 fastener holes 202 that are axially staggered as shown. The staggering allows more fasteners holes 202 to be placed in outer orifice ring 200. For larger valves, or a smaller number of fasteners, the staggering may not be needed.

Figure 13:
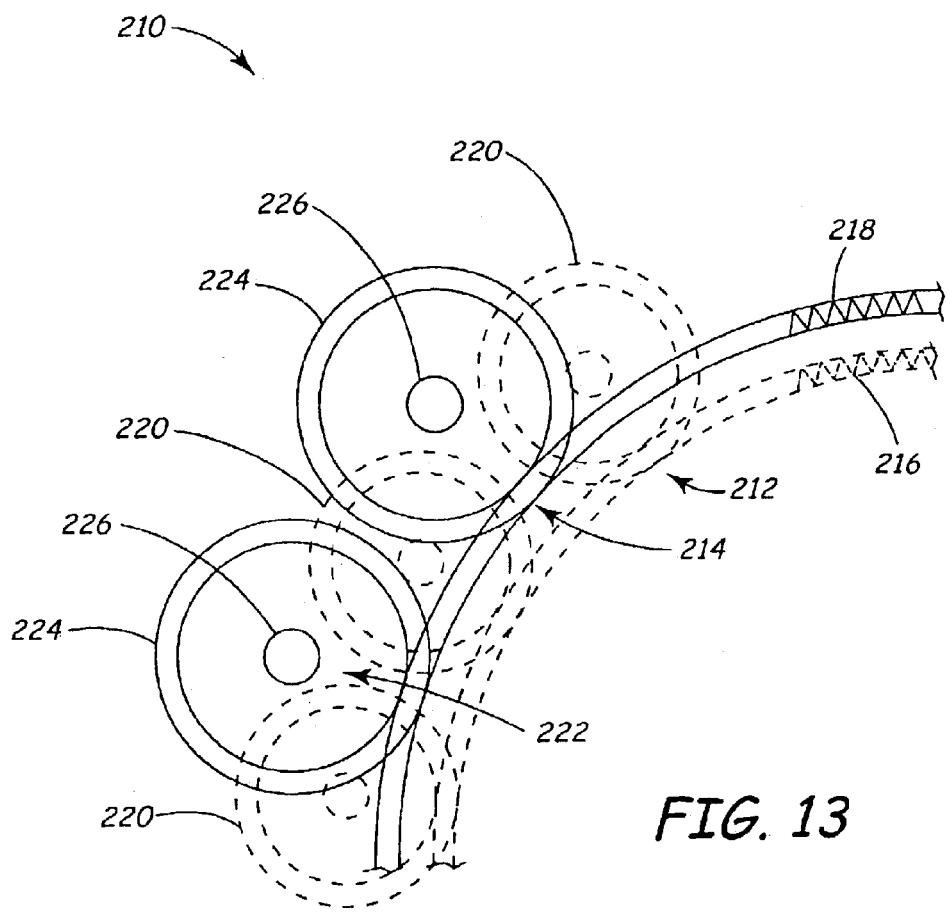
FIG. 13 is an illustration of an alternative embodiment of first and second satellite drive gear layers in a driver tool.

FIG. 13 illustrates an alternative embodiment 210 of first and second satellite drive gear layers in a driver tool. A first, or lower, drive gear layer 212 is illustrated in dashed lines, and a second, or upper drive gear layer 214 is illustrated in solid lines. The gear ratio of the first drive gear layer 212 and the second drive gear layer 214 are preferably the same. The diameter of a first drive gear 216 is slightly different than the diameter of a second drive gear 218. First satellite gears 220 are arranged as shown separated by gaps 222 between them. Second satellite gears 224 are aligned with the gaps 222 as shown.. Flexible shafts 226 of second satellite gears 224 pass between the first satellite gears 220 as illustrated. The different or staggered diameters of the drive gears 216, 218 help to position the flexible shafts 226 at a slightly larger radius where the gaps 222 are wide enough to accommodate the flexible shafts and any protruding bottom collar without rubbing on gears 220. Either the first drive gear layer 212 or the second drive gear layer 214 can be the large diameter layer, depending on the needs of the application. The first and second drive gear layers 212, 214 preferably drive all of the fasteners simultaneously at the same rate of rotation.

Figure 14:
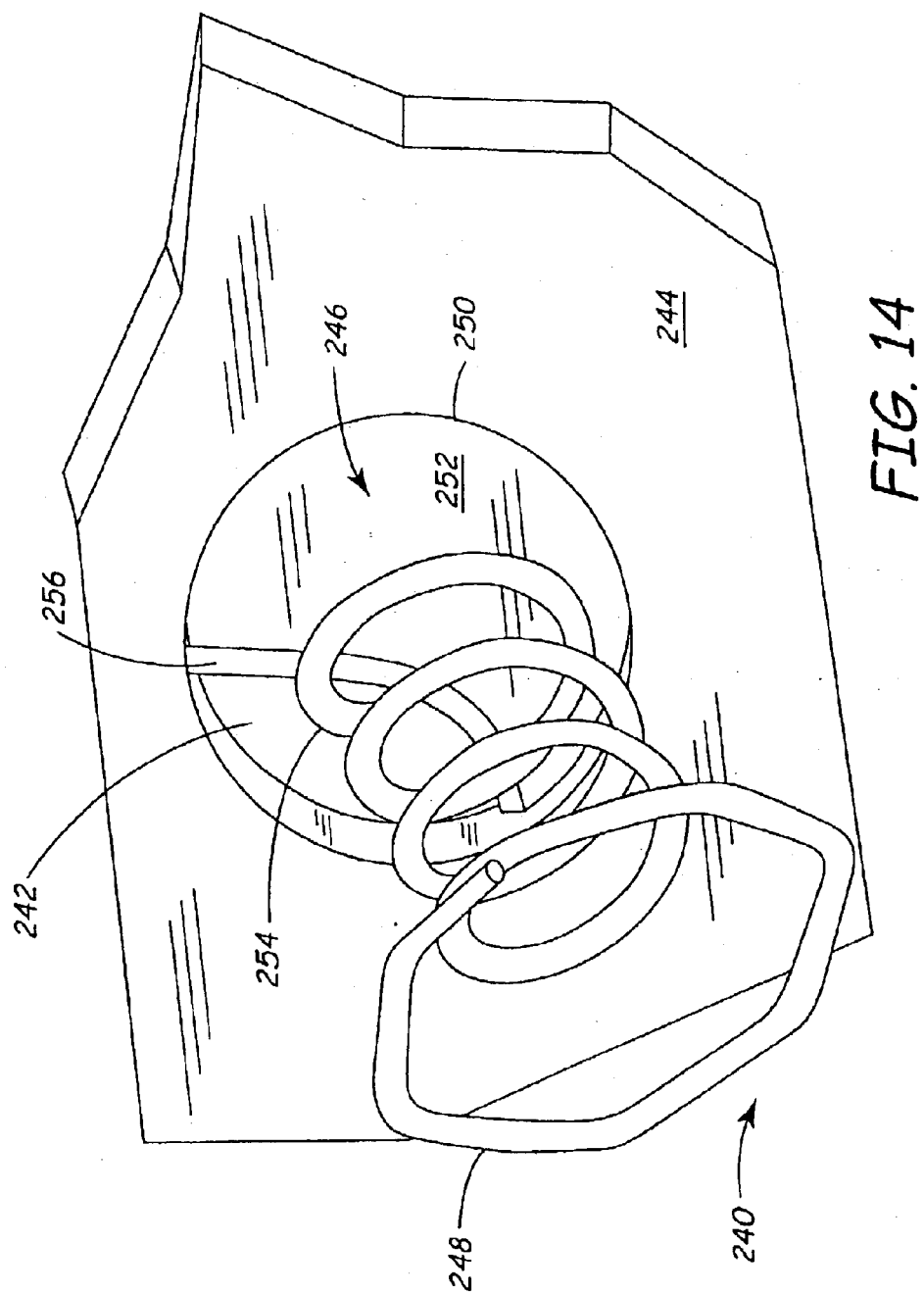
FIG. 14 is an illustration of a multiple-sided helical fastener engaging a hole in an outer orifice ring.

FIG. 14 illustrates a multiple-sided helical fastener 240 engaging a shaped hole 242 in an outer orifice ring 244. The helical fastener 240 is similar to the helical fastener 192 illustrated in FIG. 11, but does not include a generally straight section 194. Shaped hole 242 is formed in the bottom of a generally round cavity 246 that is deep enough so that a hexagonal hub portion 248 will fit in it. The outer diameter 250 of the cavity 246 is small enough so that the outer diameter of a driver tip (such as driver tip 152 illustrated in FIG. 9) is too large to enter the cavity. When the hexagonal hub portion 248 is in the cavity 246, a driver tool can not reach it, and helical fastener 240 will stop rotating, even though the driver tool continues to rotate. When the hexagonal hub portion 248 is in the cavity 246, it is disengaged from the driver tool. A plate 252 in the cavity 246 provides a seat for the hexagonal head portion 248 while the spiral portion 254 passes through the hole 242 into the tissue annulus. The plate 252 has an edge 256 that is not flat, but rounded or knife-edged. The shape of edge 256 helps to ensure that the spiral portion 254 does not catch or bind on the edge 256 Hole 242 can be relatively small and need not extend to the center of generally round cavity 246.

FIG. 15 is an illustration of the fastener 192 (FIG. 11-1) with a generally straight axial portion 194 engaging a shaped hole 270 in an outer orifice ring 272. Shaped hole 270 is sized or shaped to include the central axis of cavity 274 such that the generally straight portion 194 extends through hole 270. Shaped hole 270 is formed in the bottom of a generally round cavity 274 that is deep enough so that the hexagonal hub portion 193 will fit in it. The outer diameter 276 of the cavity 270 is small enough so that there is a space between the hexagonal hub portion 193 and the outer diameter 276.

Generally round cavity 274 (or cavity 246 in FIG. 14) can be tilted or angled slightly as illustrated in section 15-15 of FIG. 15, or generally round cavity 246, 274 can be orthogonal to the wall of outer orifice ring 244, 272. The tilt or angle can be selected to match a corresponding tilt or angle of the drive direction for the driver tool used such as in FIG. 7.

FIG. 16 is a cross-sectional illustration of a driver tip 280, the fastener 192 and the shaped hole 270 in an outer orifice ring 272, before (16-1) and after (16-2) driving the fastener 192. Driver tip 280 has a driver end 282 with a diameter that is larger than the outer diameter 276 of shaped hole 270. Driver tip 280 is too large to enter the shaped hole 270. As soon as fastener 192 is advanced beyond the driver end 282, it is disengaged from driver end 282. The driver end 282 can then spin without advancing the fastener 192 further. The arrangement shown in FIG. 16 has the advantage of automatically disengaging the fastener 192 and avoiding unnecessary twisting of the fastener 192 after it has engaged the tissue annulus. When the hexagonal hub portion 248 is in the cavity 246, a driver tool can not reach it, and helical fastener 240 will stop rotating, even though the driver tool continues to rotate. When the hexagonal hub portion 193 is in the shaped hole 270, it is disengaged from the driver end 280. Driver tip 280 can be used or adapted for use with fasteners illustrated in FIGS. 9, 11, 14 or 15.

FIG. 17 is a cross-sectional illustration of a driver tip 300, a fastener 192 and a shaped hole 270 in an outer orifice ring 272, before (17-1) and after (17-2) driving the fastener 192. Driver tip 300 has a driver end 300 with an outer diameter that is smaller than the outer diameter 276 of shaped hole 270. Driver tip 300 is small enough to enter the shaped hole 270 as illustrated. Driver tip 300 can continue to pivotally advance fastener 192 after its axial advancement relative to the shaped hole 270 has stopped. The fastener 192 spirally engages a tissue annulus which is pulled axially more tightly toward the orifice ring 272 during the pivotal advancement to provide a tighter seal between the orifice ring 272 and the tissue annulus. Leakage is thus reduced using the arrangement shown in FIG. 17. Driver tip 300 can be used or adapted for use with fasteners illustrated in FIGS. 9, 11 and 15.

The tools illustrated can be preloaded with fasteners and an outer orifice ring to form a preloaded tool-component assembly that can be packaged and sterilized for use.

Preferably, the rings set forth herein are formed of biocompatible materials such as polyethylene terephthlate (PET), polyetheretherketones (PEEK), ultrahigh molecular weight polyethylene, Nitinol® nickel-titanium alloy, polyurethane, Elgiloy® cobalt-chromium-nickel-molybdenum iron alloy, etc. (preferably more flexible than the inner ring) for the outer ring. Titanium, MP35N wrought cobalt-nickel-chromium-molybdenum alloy, ceramic, pyrolytic carbon or other rigid polymers may be used for the inner ring. The particular shapes of the orifice rings and attachment mechanisms may be modified as appropriate. The ring coupling mechanism for coupling the two rings may be any mechanism. For example, the coupling techniques may include screws, wires, bayonet locking mechanism, and nails which extend axially and engage the rings. Further, the configuration of the inner orifice ring and its occluding mechanism may be other than those set forth herein.

Implantation time is short and relatively simple implantation techniques can be used. Further, the angular positioning of the leaflets in the inner ring is easily accomplished by rotating the inner ring with respect to the outer ring. The invention allows surgical access to subvalvular features prior to coupling the inner orifice ring to the outer ring without the possibility of damaging the occluding mechanism, for example. A greater number of fasteners can be provided to decrease the spacing between attachment points. This decreased spacing reduces the likelihood of blood leakage around the implanted heart valve. The inner valve ring can be removed and replaced without excising the entire prosthesis. The complexity of surgery is reduced because manual suturing may not be required. The area of the lumen is increased over typical prior art designs and a lower profile results because the cuff attachment mechanism requires less area. With the inner ring coupled to the outer ring, the outer ring attachment mechanisms are prevented from "backing out" and completely shielded from blood flow where they could otherwise initiate formation of thrombus. Any type of occluding mechanism may be used and the attachment mechanism may be integral with the ring body. A cuff (such as a polyester cuff) may be formed on the outside of outer ring 14 to enhance implantation.

The component parts of tools depicted in FIGS. 10–17 can be constructed of biocompatible polymers such as polyurethane, acetal resin such as Delrin®, polysulfone, of metals such as stainless steel, or of other biocompatible materials. Gears are preferably constructed of nylon, polytetrafluoroethylene (PTFE) or stainless steel. The completed tool or kit can be gamma sterilized and disposable, if desired. Flexible shafts can be formed of stainless steel and coated with nylon or PTFE for lubricity. Helical screw fasteners can be made of platinum-iridium alloy, MP35N (a wrought cobalt-nickel-chromium-molybdenum alloy), stainless steel, titanium or other biocompatible materials. If desired, an electric motor can be used to provide the torsional force rather than manually twisting a handle.

Although the present invention has been described with reference to preferred embodiments, workers skilled in the art will recognize that changes may be made in form and detail without departing from the spirit and scope of the invention.

What is claimed is:

1. A driver tool for driving fasteners through fastener holes of a heart valve prosthesis component into a tissue annulus of a heart, comprising:

a tool housing having a distal housing end couplable to the component and a proximal housing end spaced away from the distal housing end along an axis;

a central shaft in the tool housing having a proximal shaft end couplable to a driving force, and having a distal shaft end;

a first satellite gear drive layer having a first drive gear engaging the distal shaft end and a first plurality of satellite gears at first spaced circumferential positions meshing with the first drive gear, and having a first plurality of flexible shafts connected to the first plurality of satellite gears and adapted to drive a first portion of the fasteners; and a second satellite gear drive layer having a second drive gear engaging the distal shaft end and a second plurality of satellite gears at second spaced circumferential positions meshing with the second drive gear, and having a second plurality of flexible shafts connected to the second plurality of satellite gears and arranged to drive a second portion of the fasteners.

2. The driver tool of claim 1 wherein the second spaced circumferential positions are circumferentially offset from the first spaced circumferential positions.

3. The driver tool of claim 1 wherein the first plurality of satellite gears are separated from one another by gaps, and the second plurality of flexible shafts pass through the gaps.

4. The driver tool of claim 3 wherein the second plurality of satellite gears are circumferentially aligned with the gaps.

5. The driver tool of claim 1 wherein the first plurality of flexible shafts and the second plurality of flexible shafts are adapted to be driven simultaneously.

6. The driver tool of claim 1 wherein the first plurality of flexible shafts and the second plurality of flexible shafts comprise at least sixteen flexible shafts adapted to drive a corresponding number of fasteners.

7. The driver tool of claim 1 further comprising:

a distributor disposed in the distal housing end and having at least one guide passageway therethrough, each one of the first and second plurality of flexible shafts passing through a corresponding guide passageway.

8. The driver tool of claim 7 wherein the fastener holes are at circumferentially spaced hole positions and the guide passageways have guide passageway ends that are aligned with the hole positions.

9. The driver tool of claim 8 wherein the fastener holes are axially staggered and the guide passageway ends are correspondingly axially staggered.

10. The driver tool of claim 1 further comprising a central distributor pin disposed in the distal housing end, and wherein each flexible shaft makes a turn inward and extends across a central region around the central distributor pin to engage a driver tip.

11. The driver tool of claim 10 wherein the turn inward is in the range of 60 to 90 degrees.

12. The driver tool of claim 1 wherein each flexible shaft makes a turn outward that avoids crossing a central region, each flexible shaft engaging a fastener.

13. The driver tool of claim 1 further comprising:

a plurality of plates arranged to support the first and second plurality of satellite gears, at least one of the plates having a plurality of radial slots extending to an outer edge of the plate; and each satellite gear being permanently assembled to a corresponding one of the flexible shafts to form a drive assembly, and each radial slot being arranged to accept a corresponding one of the drive assemblies.

14. The driver tool of claim 1 wherein:

each fastener has a helical first portion wound around a helical axis and a generally straight second portion extending along the helical axis and adapted to rotate in the fastener hole, and a third flat portion;

the first and second plurality of flexible shafts have slotted shaft ends adapted to selectively drive the third flat portion of each fastener; and each fastener being adapted to selectively advance relative to the fastener hole when the helical portion passes through the fastener hole, and being adapted to selectively rotate in the fastener hole when the straight second portion engages the heart valve prosthesis component.

15. The driver tool of claim 14 wherein the slotted shaft ends are adapted to rotate the fasteners when the flat third portion engages the heart valve prosthesis component, drawing the tissue annulus toward the heart valve prosthesis component.

16. The driver tool of claim 1 wherein:

each fastener has a spiral wire wound around a spiral axis, the spiral wire winding on a generally circular path along its length and having an N-sided end turn joined to the spiral wire; and the first and second plurality of flexible shafts have shaft ends having N-sided sockets adapted to slidingly engage the N-sided end turn and adapted to slide over the spiral wire.

17. The driver tool of claim 16 wherein N is a number selected in the range of 3 to 8.

18. The driver tool of claim 1 wherein:

each fastener has an auger-shaped first portion adapted to engage the tissue annulus and an M-sided second portion; and the first and second plurality of flexible shafts each having shaft ends having M-sided sockets adapted to slidingly engage the M-sided second portions of each fastener and adapted to slide over the auger-shaped first portion.

19. The driver tool of claim 1 and further comprising the heart valve prosthesis component and the fasteners, the fasteners engaging the fastener holes and flexible shaft ends to form a preloaded tool assembly.

20. A method of attaching a heart valve prosthesis component to a tissue annulus of a heart with fasteners, comprising:

providing a driver tool having a distal end couplable to the component and a proximal end spaced away from the distal end along an axis;

providing a two tier gear drive in the driver tool adapted to couple a drive force at the proximal end to multiple driver tips at the distal end;

providing a heart valve prosthesis component with fastener holes;

providing fasteners coupled to the driver tips and passing through the fastener holes;

placing the component in contact with the tissue annulus;

advancing the fasteners into the tissue annulus by providing the drive force at the proximal end of the driver tool; and removing the driver tool from the component, leaving the component attached to the tissue annulus by the fasteners.

21. The method of claim 20, further comprising:

pulling up a handle to retract the driver tips.

22. A kit for attaching a heart valve prosthesis component to an annulus of tissue in a heart, comprising:

a heart valve prosthesis component;

a driver tool having a handle extending from a drive shaft on a proximal end and distributing drive through first and second stacked satellite gear drive layers to a plurality of driver tips on a distal end of the driver tool, the distal end being removably attached to the heart valve prosthesis component; and a plurality of fasteners passing through holes in the heart valve prosthesis component, each of the fasteners removably coupling to one of the plurality of driver tips.

* * * * *